United States Patent [19]
Suda

[11] Patent Number: 5,409,485
[45] Date of Patent: Apr. 25, 1995

[54] POWER SUPPLY APPARATUS FOR ELECTROSURGICAL UNIT INCLUDING ELECTROSURGICAL-CURRENT WAVEFORM DATA STORAGE

[75] Inventor: Masao Suda, Yaita, Japan

[73] Assignee: Kabushiki Kaisha Toshiba, Kawasaki, Japan

[21] Appl. No.: 70,927

[22] Filed: Jun. 4, 1993

Related U.S. Application Data

[62] Division of Ser. No. 637,196, Jan. 3, 1991, Pat. No. 5,290,283.

[30] Foreign Application Priority Data

Jan. 31, 1990 [JP] Japan ................................. 2-20792
Mar. 5, 1990 [JP] Japan ................................. 2-51893

[51] Int. Cl.$^6$ ............................................. A61B 17/39
[52] U.S. Cl. .......................................... 606/34; 606/37
[58] Field of Search ....................... 606/32, 34, 37–40, 606/46, 47

[56] References Cited

U.S. PATENT DOCUMENTS

| | | | |
|---|---|---|---|
| 4,517,976 | 5/1985 | Murakoshi | 606/46 |
| 4,716,897 | 1/1988 | Noguchi et al. | 606/34 |
| 4,742,815 | 5/1988 | Ninan et al. | 606/39 X |
| 5,056,503 | 10/1991 | Nagasaki et al. | 606/46 X |

FOREIGN PATENT DOCUMENTS

| | | | |
|---|---|---|---|
| 3923024 | 2/1990 | Germany | 606/37 |
| 2154881 | 9/1985 | United Kingdom | 606/37 |

*Primary Examiner*—Lee S. Cohen
*Attorney, Agent, or Firm*—Oblon, Spivak, McClelland, Maier, & Neustadt

[57] ABSTRACT

In an electrosurgical power supply apparatus combined with an electronic endoscope system, there is provided an electrosurgical signal generator. The electrosurgical signal generator includes PROM for previously storing data representative of electrosurgical high-frequency currents. In response to a selection signal of an electrosurgical operation mode, the data is read out from PROM to produce the electrosurgical high-frequency current corresponding to the selected electrosurgical operation mode.

11 Claims, 15 Drawing Sheets

FIG. 5

| | 00 | 01 | 02 | 03 | 04 | 05 | 06 | 07 | 08 | 09 | 0A | 0B | 0C | 0D | 0E | 0F |
|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | 0 |
| 1 | 1 | 0 | 0 | 0 | 0 | 0 | 0 | 0 | 0 | 0 | 0 | 0 | 0 | 0 | 0 | 0 |
| 2 | 1 | 1 | 0 | 0 | 0 | 0 | 0 | 0 | 0 | 0 | 0 | 0 | 0 | 0 | 0 | 0 |
| 3 | 1 | 1 | 1 | 0 | 0 | 0 | 0 | 0 | 0 | 0 | 0 | 0 | 0 | 0 | 0 | 0 |
| 4 | 1 | 1 | 1 | 1 | 0 | 0 | 0 | 0 | 0 | 0 | 0 | 0 | 0 | 0 | 0 | 0 |
| 5 | 1 | 1 | 1 | 1 | 1 | 0 | 0 | 0 | 0 | 0 | 0 | 0 | 0 | 0 | 0 | 0 |
| 6 | 1 | 1 | 1 | 1 | 1 | 1 | 0 | 0 | 0 | 0 | 0 | 0 | 0 | 0 | 0 | 0 |
| 7 | 1 | 1 | 1 | 1 | 1 | 1 | 1 | 0 | 0 | 0 | 0 | 0 | 0 | 0 | 0 | 0 |
| 8 | 1 | 1 | 1 | 1 | 1 | 1 | 1 | 1 | 0 | 0 | 0 | 0 | 0 | 0 | 0 | 0 |
| 9 | 1 | 1 | 1 | 1 | 1 | 1 | 1 | 1 | 1 | 0 | 0 | 0 | 0 | 0 | 0 | 0 |
| A | 1 | 1 | 1 | 1 | 1 | 1 | 1 | 1 | 1 | 1 | 0 | 0 | 0 | 0 | 0 | 0 |
| B | 1 | 1 | 1 | 1 | 1 | 1 | 1 | 1 | 1 | 1 | 1 | 0 | 0 | 0 | 0 | 0 |
| C | 1 | 1 | 1 | 1 | 1 | 1 | 1 | 1 | 1 | 1 | 1 | 1 | 0 | 0 | 0 | 0 |
| D | 1 | 1 | 1 | 1 | 1 | 1 | 1 | 1 | 1 | 1 | 1 | 1 | 1 | 0 | 0 | 0 |
| E | 1 | 1 | 1 | 1 | 1 | 1 | 1 | 1 | 1 | 1 | 1 | 1 | 1 | 1 | 0 | 0 |
| F | 1 | 1 | 1 | 1 | 1 | 1 | 1 | 1 | 1 | 1 | 1 | 1 | 1 | 1 | 1 | 0 |

Columns: OUTPUTS FROM 2ND COUNTER 15 / LOWER 4-BIT ADDRESS OF 1ST PROM 17
Rows: POWER SETTING PULSE / UPPER 4-BIT ADDRESS OF 1ST PROM 17

FIG. 6

| | 00 | 01 | 02 | 03 | 04 | 05 | 06 | 07 | 08 | 09 | 0A | 0B | 0C | 0D | 0E | 0F |
|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | 0 |
| 1 | 0 | 0 | 0 | 0 | 0 | 0 | 0 | 0 | 0 | 0 | 0 | 0 | 0 | 0 | 0 | 0 |
| 2 | 1 | 1 | 1 | 1 | 1 | 1 | 1 | 1 | 0 | 0 | 0 | 0 | 0 | 0 | 0 | 0 |
| 3 | 0 | 0 | 0 | 0 | 2 | 0 | 0 | 0 | 0 | 0 | 0 | 0 | 0 | 0 | 0 | 0 |
| 4 | 1 | 1 | 1 | 1 | 1 | 1 | 0 | 0 | 0 | 0 | 0 | 0 | 0 | 0 | 0 | 0 |
| 5 | 0 | 0 | 0 | 0 | 2 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 0 | 0 | 0 | 0 | 0 | 0 |
| 8 | 1 | 1 | 1 | 0 | 2 | 0 | 0 | 0 | 0 | 0 | 0 | 0 | 0 | 0 | 0 | 0 |
| 9 | 0 | 0 | 0 | 0 | 0 | 0 | 0 | 0 | 0 | 0 | 0 | 0 | 0 | 0 | 0 | 0 |
| A | 0 | 0 | 0 | 0 | 0 | 0 | 0 | 0 | 0 | 0 | 0 | 0 | 0 | 0 | 0 | 0 |
| B | 0 | 0 | 0 | 0 | 0 | 0 | 0 | 0 | 0 | 0 | 0 | 0 | 0 | 0 | 0 | 0 |
| C | 0 | 0 | 0 | 0 | 0 | 0 | 0 | 0 | 0 | 0 | 0 | 0 | 0 | 0 | 0 | 0 |
| D | 0 | 0 | 0 | 0 | 0 | 0 | 0 | 0 | 0 | 0 | 0 | 0 | 0 | 0 | 0 | 0 |
| E | 0 | 0 | 0 | 0 | 0 | 0 | 0 | 0 | 0 | 0 | 0 | 0 | 0 | 0 | 0 | 0 |
| F | 0 | 0 | 0 | 0 | 0 | 0 | 0 | 0 | 0 | 0 | 0 | 0 | 0 | 0 | 0 | 0 |

Rows 2–3: BLEND-1
Rows 4–5: BLEND-2
Rows 8–9: COAG.

Row labels (left column): MODE SELECTING PULSE / UPPER 3-BIT ADDRESS OF 2ND PROM 18

Column headers (top): OUTPUTS FROM 3RD COUNTER 16 / LOWER 5-BIT ADDRESS OF 2ND PROM 18

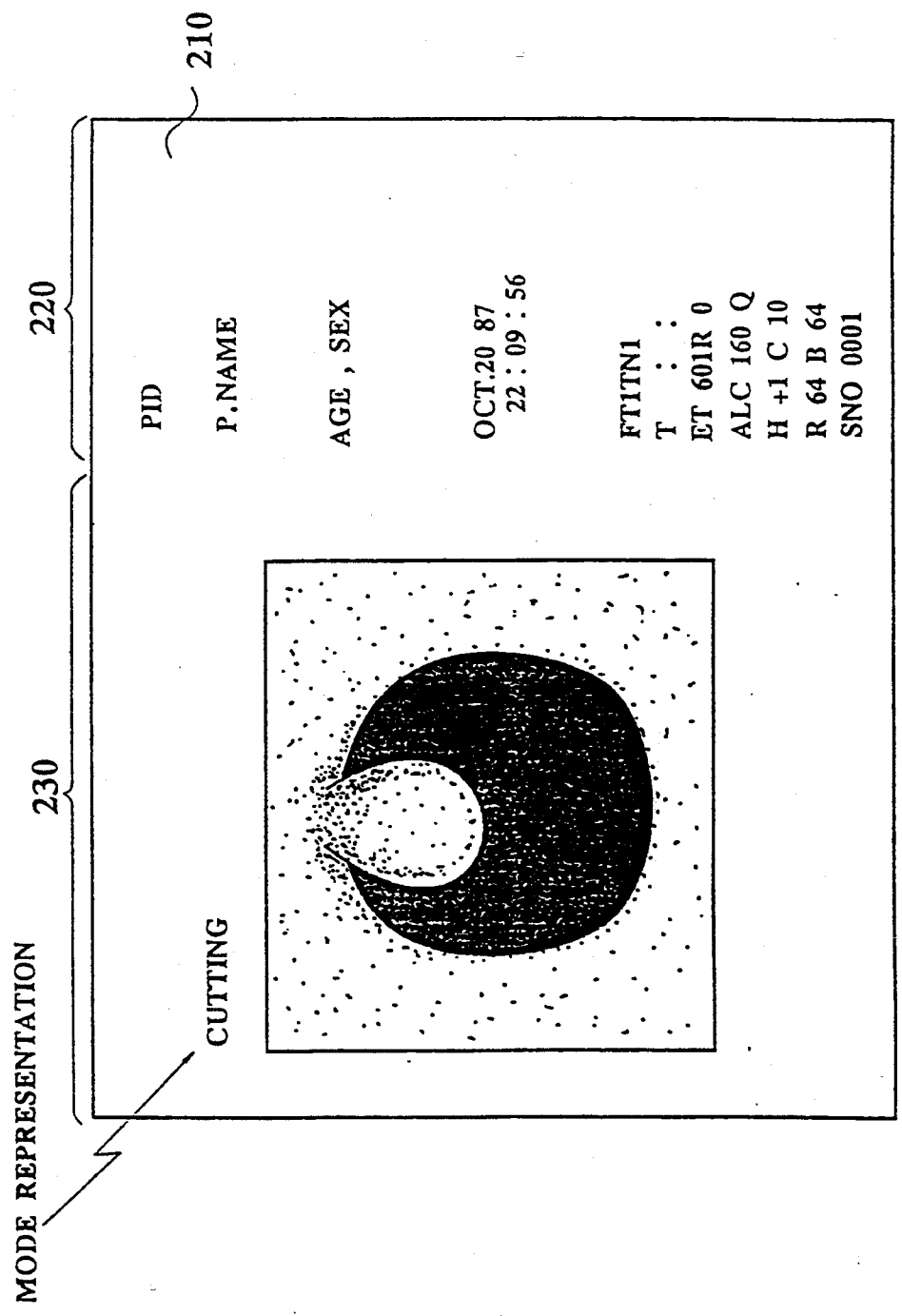

FIG. 15A CUT
FIG. 15B BLEND
FIG. 15C COAG

POWER SUPPLY APPARATUS FOR ELECTROSURGICAL UNIT INCLUDING ELECTROSURGICAL-CURRENT WAVEFORM DATA STORAGE

This is a division of application Ser. No. 07/637,196, filed on Jan. 3, 1991, now U.S. Pat. No. 5,290,283.

BACKGROUND OF THE INVENTION

1. Field of the Invention

The present invention generally relates to a power supply apparatus for an electrosurgical unit, or high frequency surgical equipment.

More specifically, the present invention is directed to an electrosurgical power supply apparatus capable of previously storing electrosurgical-current waveform data and also capable of distinguishably displaying operation modes.

2. Description of the Related Art

In general, an electrosurgical unit has a major function to achieve surgical invasion. There are typical three electrosurgical operation modes: A) COAGULATION B) CUTTING, and C) BLEND (CUTTING and COAGULATION). When a biological body such as a patient is subject to the three operation modes, both variations in a tissue of the biological body and curing histories thereof are identical to each other. There is another merit of such an electrosurgical operation (electrosurgery) that an amount of hemostasis is rather small and blood absorption from wounded portions of a biological body is also low.

Therefore, very recently, electrosurgical units with the above-described merits have been widely utilized in conjunction with electronic endoscope apparatuses so as to perform polypectomy and hemostasis, while observing a body cavity of a biological body by the electronic endoscope apparatus. Accordingly, an electronic endoscope apparatus was aimed to perform diagnosis to a biological body in the initial developing stage of the endoscope apparatus. However, the major purposes of the recently developed endoscope apparatus are to not only diagnose the biological body, but also to cure a lesion within the biological body which has been discovered during the endoscopic examination. In particular, there is an absolute need for executing polypectomy and judging whether this cut polyp is subject to a cancer or not during the recent endoscopic examination. Under such circumstances, an electrosurgical operation has an extreme merit for performing the polypectomy. To cure a lesion of a biological body by way of an electronic endoscope apparatus in conjunction with an electrosurgical unit, a high-frequency electrosurgical current produced from an electrosurgical power supply apparatus is supplied through a forceps channel of an endoscopic scope thereof to a snare of the electrosurgical unit, thereby electrosurgically cutting the lesion between the snare and return electrode.

In accordance with one conventional electrosurgical power supply apparatus, a plurality of monostable multivibrators have been employed in an electrosurgical signal generating unit so as to produce desired high-frequency current waveforms. However, this conventional electrosurgical power supply apparatus has the following drawbacks.

That is, since the monostable multivibrator is generally constructed of a circuit combination between a resistor and a capacitor, and an active element so as to form a high-frequency signal current, desirable signal waveforms are not always produced. In other words, shapes of the output signals from the monostable multivibrator are not always constant even if the values (i.e. time constant) of these resistor and capacitor are preset. Moreover, since plural monomultivibrators are employed to selectively set the sorts of the electrosurgical operations such as cutting and coagulation modes, a lengthy time required for adjusting the time constant setting elements is needed. In addition, a resultant size of an electrosurgical power supply apparatus becomes large if a signal generating unit employs a plurality of monostable multivibrators. Accordingly, there is a problem not to satisfy a need for integrally assembling both the endoscopic apparatus and electrosurgical power supply apparatus within a single unit. Furthermore, as previously described, since the waveforms of the signals produced from the monostable multivibrator signal generators are not always constant in a preselected electrosurgical operation mode, reliabilities of this electrosurgical power supply apparatus become low.

As previously stated, since many proposals have been made to incorporate an electrosurgical power supply apparatus into an electronic endoscope apparatus as a single unit, there are many possibilities to install such a combination unit within narrower medical examination rooms or spaces.

On the other hand, in general, a large quantity of switches, dials, push buttons and the likes are provided on display panels of the conventional electronic endoscope apparatuses. If other switches and dials of the electrosurgical unit are additionally employed on the display panel of the electronic endoscope apparatus, the entire display panel having such switches and dials becomes complex. Furthermore, there is another difficulty, namely there are regulations such as JIS (Japanese Industrial Safety) and IEC to indicate these components based upon the electrosurgical modes in different colors. For instance, the push buttons used for both the cutting and coagulation modes must be colored in yellow and blue, respectively, based on the IEC regulation. As previously described, since the push buttons and switches are provided under complex conditions, it is rather difficult to distinguish these members by colors for any operators of electronic endoscope apparatus equipped with electrosurgical units. More specifically, since these components gradually become dirty after the lapse of time, such color distinguishabilities are considerably deteriorated.

On the other hand, while observing the television monitor of the conventional electronic endoscope apparatus, an operator proceeds with the endoscopic examination. Under such a circumstance, he can hardly check whether or not the correct push buttons are manipulated by him.

The present invention has been made in an attempt to solve the above-described problems belonging to the conventional electrosurgical power supply apparatuses, and therefore has a primary object to provide an electrosurgical power supply apparatus capable of correctly producing desirable high-frequency electrosurgical current waveforms, and also of generating such preferable waveforms under simple operation.

A further object of the present invention is to provide an electrosurgical power supply apparatus capable of preventing erroneous operations of these switch/dial members even in a combination between an electronic endoscope apparatus and this electrosurgical power supply apparatus.

SUMMARY OF THE INVENTION

The above-described objects may be achieved by providing an electrosurgical power supply apparatus (20) comprising:

electrosurgical signal generator means (40:50:60) including at least:

data storage means (17:18:52:54:62) for previously storing therein data representative of an electrosurgical high-frequency signal; and data processing means (19) for reading the data stored in the data storage means to produce an electrosurgical high-frequency current having a waveform suitable to a selected electrosurgical operation mode.

BRIEF DESCRIPTION OF THE DRAWINGS

The accompanying drawings illustrates the present invention, in which:

FIGS. 5 and 6 represent ROM data for first and second PROMs shown in FIG. 3;

FIG. 15A through 15C are the waveforms used for the display of FIG. 14.

DETAILED DESCRIPTION OF THE PREFERRED EMBODIMENTS

Basic Ideas

Roughly speaking, the electrosurgical power supply apparatus according to the present invention has been made based upon two basic ideas.

In an electrosurgical power supply apparatus, according to a first basic idea of the present invention, for driving an electrosurgical snare by a high frequency current so as to perform surgical invasion to a biological body, there is provided signal generating means in which electrosurgical data have been previously written into storage elements and the electrosurgical data are read out therefrom in order to produce a high-frequency electrosurgical current waveform suitable for the selected electrosurgical operation mode.

In accordance with the electrosurgical-power supply apparatus with the above-described arrangement based upon the first basic idea, the electrosurgical data are read out from the storage elements of the signal generating means, whereby a desirable, high-frequency electrosurgical current corresponding to the electrosurgical operation mode may be produced. Thus, since this high-frequency electrosurgical current is supplied to the snare, the correct electrosurgery may be realized in the desirable electrosurgical operating mode. In other words, the electrosurgical current having such a desirable, correct waveform may be continuously produced in the selected electrosurgical operation mode from the electrosurgical power supply apparatus according to the first basic idea.

Furthermore, in an electrosurgical power supply apparatus, according to a second basic idea of the present invention, equipped with switches and operation dials, to which different functional representations must be attached in the light of legal regulation, there is provided operation mode representing means for representing an electrosurgical operation mode on a monitor screen while these operation dials and switches are manipulated.

According to the electrosurgical power supply apparatus of the second basic idea, since the selected electrosurgical operation mode is represented when the operation dials and switches corresponding to this selected mode are manipulated, any operator may readily recognize which the electrosurgical operation mode has been selected from the monitor screen.

Accordingly, even when this electrosurgical power supply apparatus is incorporated into an electronic endoscopic apparatus having complex arrangements of operating dials as well as switches, any operator may easily recognize the presently operated electrosurgical modes.

Figure 1:
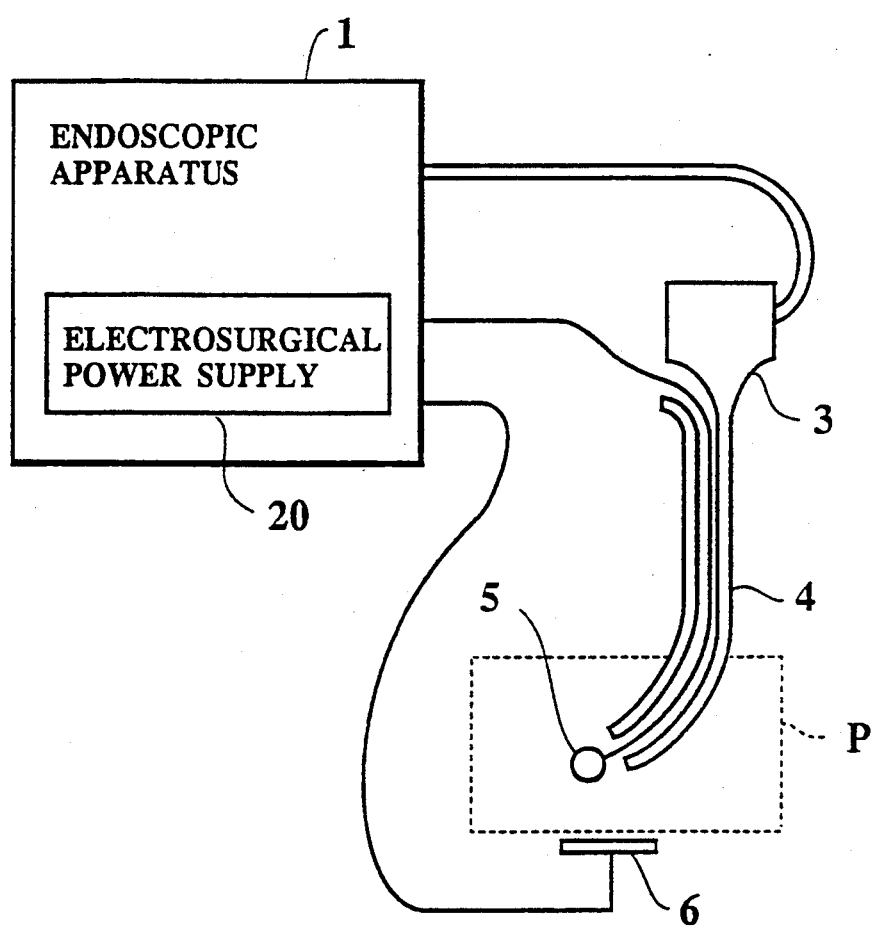
FIG. 1 schematically illustrates a first power supply apparatus 20 for an electrosurgical unit incorporated into an endoscopic apparatus, according to a preferred embodiment of the present invention.

Overall Arrangement of First Electrosurgical Power Supply Apparatus Incorporated Into Endoscopic Apparatus Referring now to FIG. 1, an electrosurgical power supply apparatus 20, constructed based upon the above-described first basic idea, incorporated into an electronic endoscope apparatus 1 will be described.

As apparent from this figure, both the first electrosurgical power supply apparatus 20 and electronic endoscope apparatus 1 have been made in an integral unit. A snare electrode 5 is conducted through a forceps channel 4 of an endoscopic scope 3 to a tip portion of this endoscopic scope 3 which is connected to a main body of this electronic endoscope apparatus 1. This snare 5 is electrically connected to the electrosurgical power supply apparatus 20 so as to be driven by high-frequency electrosurgical current. A return electrode 6 is provided on a biological body "P" such as a patient, opposite to the snare 5. Accordingly, a closed circuit of the first electrosurgical power supply apparatus 20 is formed by these snare electrode 5 and return electrode 6 via the biological body "P".

Circuit Arrangement of First Electrosurgical Power Supply Apparatus

Figure 2:
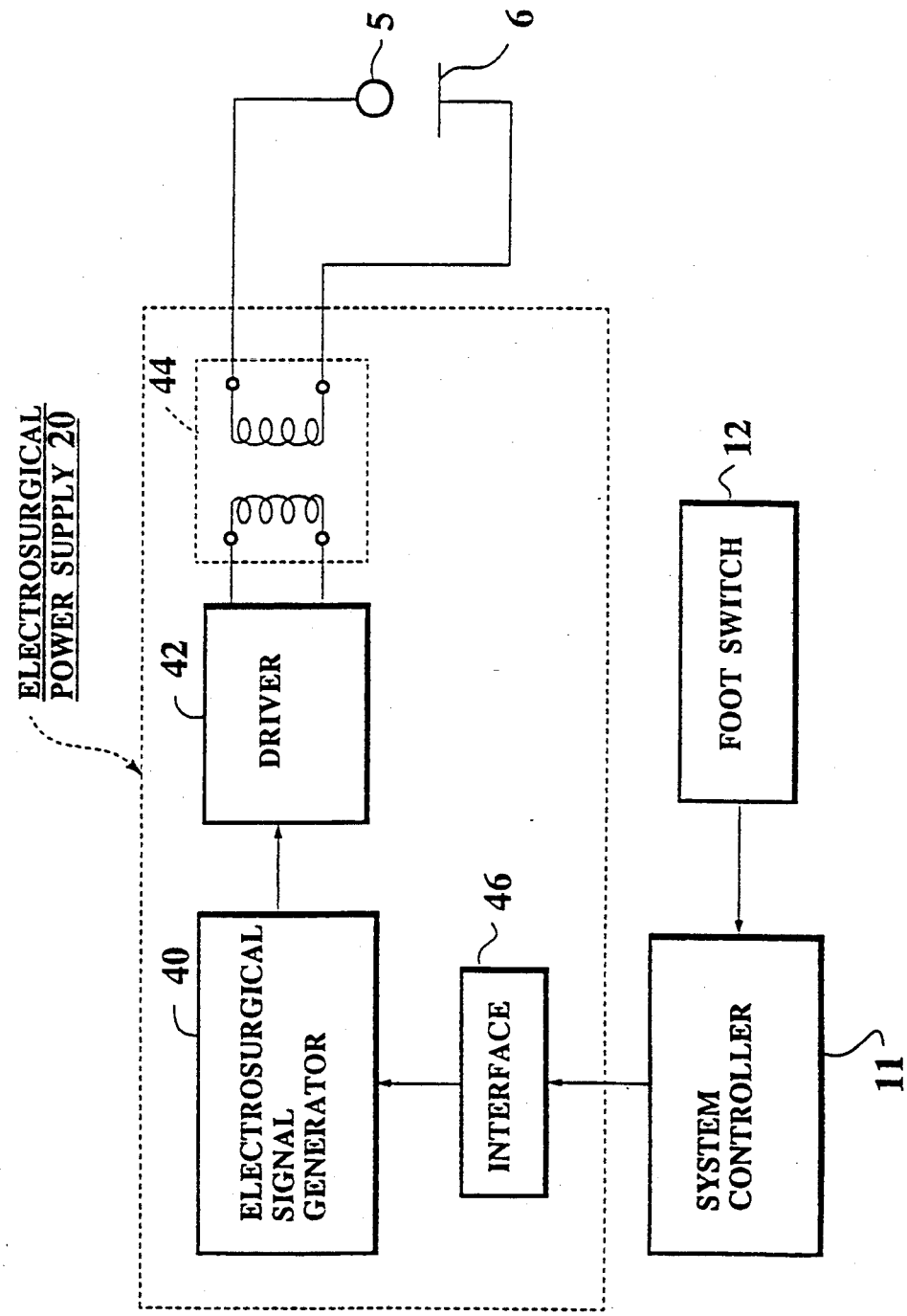
FIG. 2 is a schematic block diagram of an internal arrangement of the first electrosurgical power supply apparatus shown in FIG. 1.

FIG. 2 is a schematic block diagram for representing an overall construction of a first electrosurgical power supply apparatus 20 arranged based upon the above-described first basic idea of the present invention. The first electrosurgical power supply apparatus 20 is mainly constructed of an electrosurgical signal generating unit 40, a driver 42, an output transformer 44, and an interface unit 46. An overall system of this electrosurgical signal generating unit 40 is controlled by a system controller 11 which is commonly used by the electronic endoscope apparatus 1 shown in FIG. 1. Also, to this system controller 11, a foot switch 12 is connected.

Figure 3:
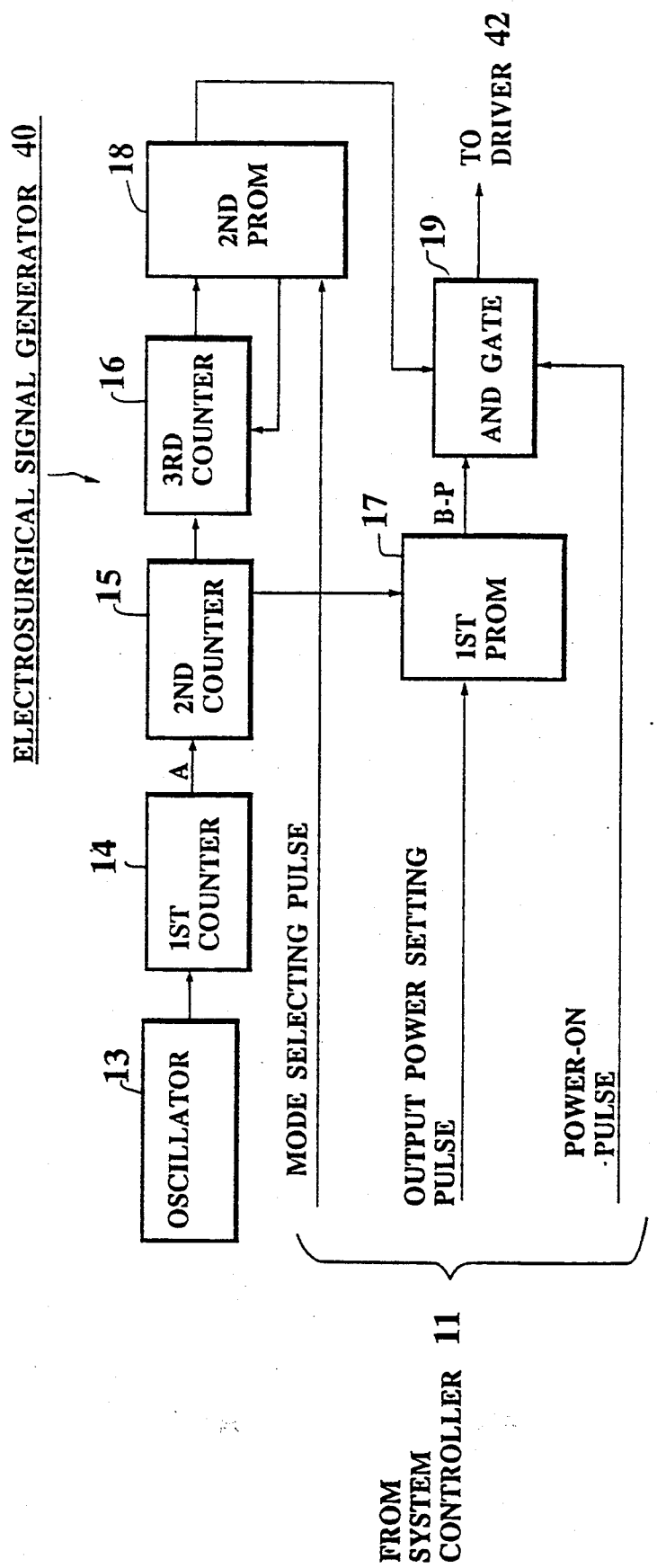
FIG. 3 is a schematic block diagram of an internal circuit of the electrosurgical signal generator 40 shown in FIG. 2.

Internal Circuit Arrangement of First Electrosurgical Power Supply Apparatus The electrosurgical signal generating unit 40 constitutes a major portion of the first electrosurgical power supply apparatus 20. This signal generating unit 40 is arranged by an oscillator 13, a first counter 14, a second counter 15, a third counter 16, a first PROM (programmable read-only memory) 17, a second PROM 18, and an AND gate 19, as represented in FIG. 3.

Figure 4:
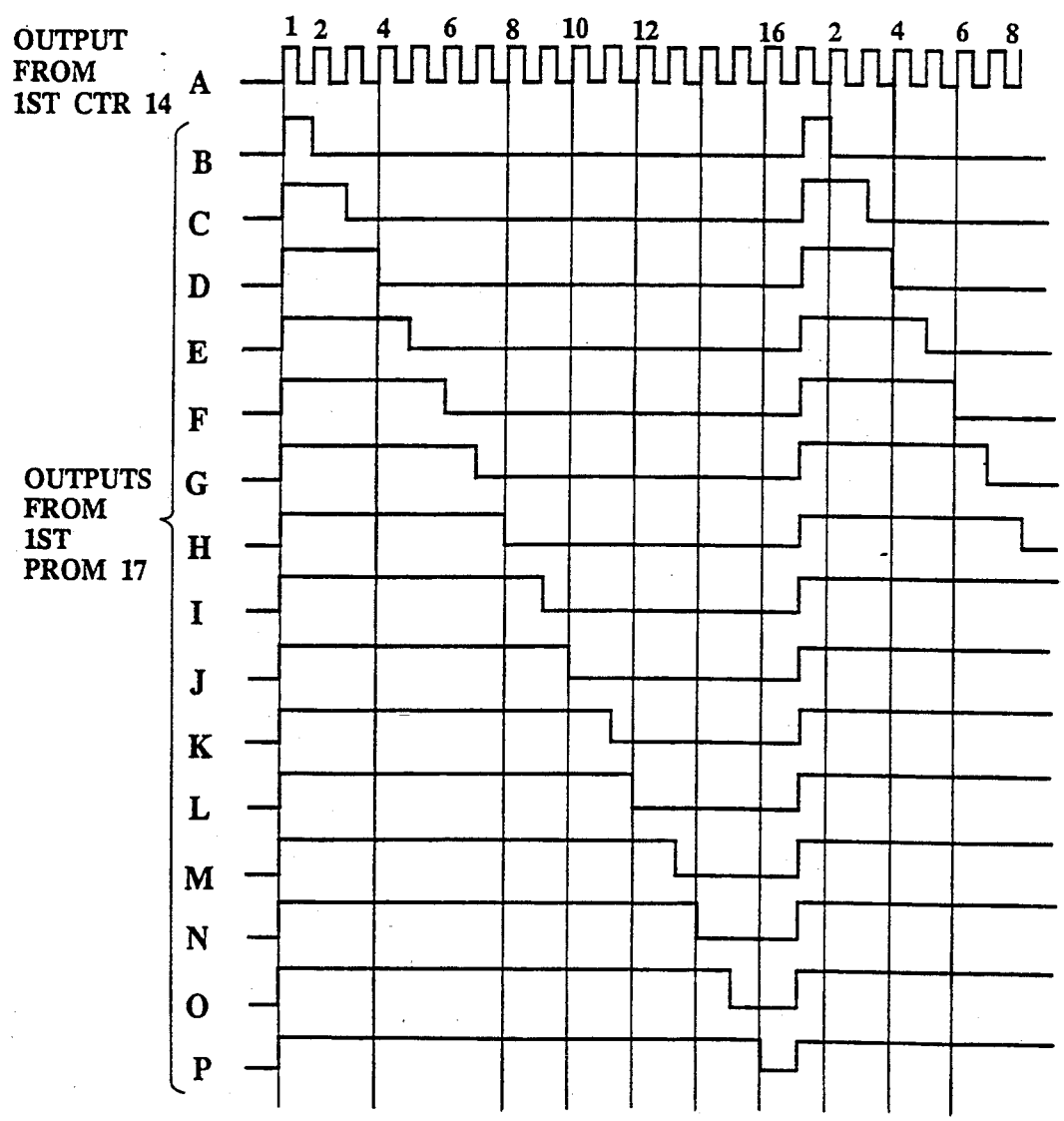
FIG. 4 is a waveform chart for explaining operation of the electrosurgical signal generator 4.

The oscillator 13 may be constructed of high-frequency signal oscillator such as a crystal oscillator and a ceramics oscillator. When a high-frequency signal outputted from the oscillator 13 is supplied to the first counter 14, a counter output signal having a waveform as shown in a symbol "A" of FIG. 4, is supplied from the first counter 14 to the second counter 15. This second counter 15 is arranged by, for instance, a 4-bit counter. One output terminal of this second counter 15 is connected to, for instance, a lower 4-bit address of the first PROM 17, and the other output terminal of the second counter 15 is connected to an input terminal of the third counter 16 constituting as a carry-bit input terminal.

A 4-bit output power setting pulse is supplied from the system controller 11 through the interface unit 10 shown in FIG. 2, to the upper address bits 5 to 8 of the first PROM 17. On the other hand, ROM data as represented in FIG. 5 have been previously written into the first PROM 17. Accordingly, in response to the 4-bit output power setting pulse, PROM outputs represented by symbols "B" to "P" shown in FIG. 4 are derived from the first PROM 17. It should be noted that since an output "0" of this PROM 17 is omitted, 15 sorts of PROM outputs are represented. In FIG. 5, an abscissa denotes lower 4-bit address of the first PROM 17, whereas an ordinate indicates upper 4-bit address thereof. The upper 4-bit data shown in FIG. 5 is to select a pulse width of the ROM output, as apparent from FIG. 4. For instance, when 3rd address of the upper address represented in the ordinate of FIG. 5 is selected by the output power setting pulse, outputs having "1" are derived from the first PROM 17 from address "00" to address "02" of the lower address shown in the abscissa. That is to say, a waveform of the power output derived from the first PROM 17 corresponds to a waveform "D" of the PROM output shown in FIG. 4. As previously described, a width of the rectangular PROM output may be determined by the output power setting pulse, namely the upper 4-bit address data of the first PROM 17.

It should also be noted that although the above-described output power setting signal has been selected to be 4 bits, i.e., 16 signal stages, other different bits may be, of course, employed.

The third counter 16 is made of, for instance, a 5-bit counter, and an output terminal thereof is connected to lower 5-bit address terminals of the second PROM 18. To upper address bits 6–8 of the second PROM 18, a mode selecting pulse is similarly supplied from the system controller 11 via the interface unit 10 of FIG. 2. One output terminal of the second PROM 18 is connected to a reset terminal of the third counter 16. Similarly, ROM data as shown in FIG. 6 have been previously written into the second PROM 18, so that outputs having waveforms as shown in FIG. 7 are derived from the other output terminal of this second PROM 18.

As apparent from FIG. 6, a lower 5-bit-address of the second PROM 18 is denoted by two columns of the abscissa, whereas an upper 3-bit address is indicated in a single row of the ordinate. It should be noted that the reason why the ROM data at 34 address, 54 address and 94 address are equal to "2", is to reset the third counter 16 at the second bit of each PROM output.

Figure 7:
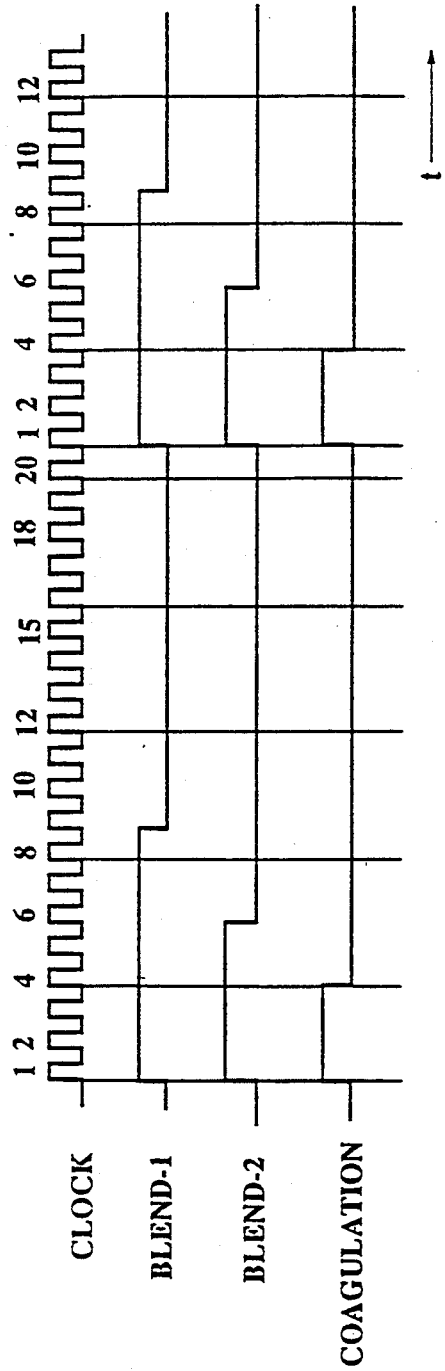
FIGS. 7 and 8 are waveform charts for explaining operations of the electrosurgical modes.

FIG. 7 is a timing chart for denoting various operations of the second PROM 18.

In this timing chart, for instance, to select a blend mode "BLEND-1" having two functions of cutting and coagulation, "001" are supplied to the upper 3-bit addresses of the second PROM 18. As a result, the item (ROM data) of the BLEND-1 shown in FIG. 6 is selected and the waveform denoted by "BLEND-1" shown in FIG. 7 is obtained. In this case, the PROM output at the address of "34" is equal to "2" as represented in FIG. 6. This output "2" is used to reset the third counter 16. The third counter 16 repeats its counting operation when the count value becomes 20. It should be noted that other count value than 20 of the third counter 16 may be select.

As apparent from the foregoing description, a relationship between the output from the first PROM 17 and the output from the second PROM 19 is such that one clock shown in FIG. 7 corresponds to one clock as represented in FIG. 4. Then, the outputs from the respective first PROM 17 and second PROM 18 are furnished to the AND gate 19. Furthermore, when the input operation is performed by, for example, the foot switch 12 shown in FIG. 2, a power-ON pulse for commencing a surgical operation is supplied via the interface unit 10 from the system controller 11 shown in FIG. 2 to the AND gate 19.

Figure 8:
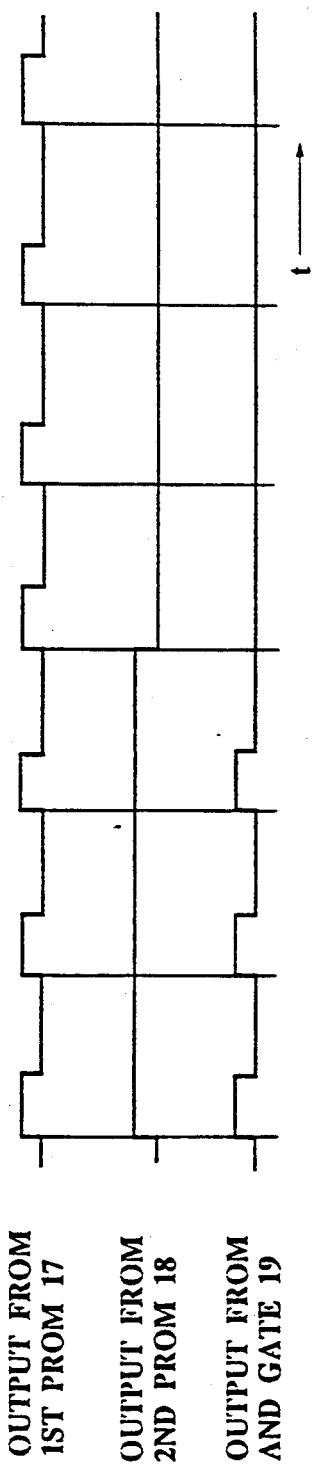

Then, after the outputs from both the first and second PROMs 17 and 18, and the power-ON pulse are AND-gated in the AND gate 19, the coagulation output, for instance, is derived from this AND gate 19 at a predetermined timing as shown in FIG. 8. This coagulation output from the AND gate 19 is supplied to control the driver 42 shown in FIG. 2, so that the output transformer 44 supplies the high-frequency electrosurgical current having the coagulation waveform as shown in FIG. 8 to the snare electrode 5. Accordingly, electrosurgery may be performed in the selected coagulation mode by way of the snare electrode 5 and return (dispersive) electrode 6. It should be noted that a portion of 20 clock pulses outputted from the second PROM 18 shown in FIG. 7 is enlarged in the timing chart of FIG. 8, and also the actual high-frequency current waveform outputted from the driver 42 is repeated in a unit of 20 pulses.

When, on the contrary, the upper address bits of the first and second PROMs 17 and 18 are not selected, namely when no electrosurgical operation mode is designated, both outputs of these PROMs 17 and 18 become zero, as apparent from the ROM data shown in FIGS. 5 and 6. As a result, no high-frequency electrosurgical current is outputted from the senar 5 so that erroneous electrosurgical operation may be prevented. It should be understood that the ROM data of the first and second PROMs 17 and 18 are not limited to those shown in FIGS. 5 and 6, but may be variously modified.

As previously explained, in accordance with the first electrosurgical power supply apparatus 20, the ROM data which have been previously written into the first and second PROMs 17 and 18 are selectively read out therefrom in order to produce the proper high-frequency electrosurgical current, depending upon the selected electrosurgical operation mode.

Since the electrosurgical signal generating unit 40 capable of generating such a proper high-frequency electrosurgical current is assembled in the electrosurgical power supply apparatus 20, the compact electrosurgical power supply apparatus 20 may be made. As a consequence, it is very easy to integrate, or incorporate such a compact electrosurgical power supply apparatus 20 into the electronic endoscope apparatus 1 shown in FIG. 1.

Practical Circuit Diagram of First Electrosurgical Power Supply Apparatus

Figure 9A:
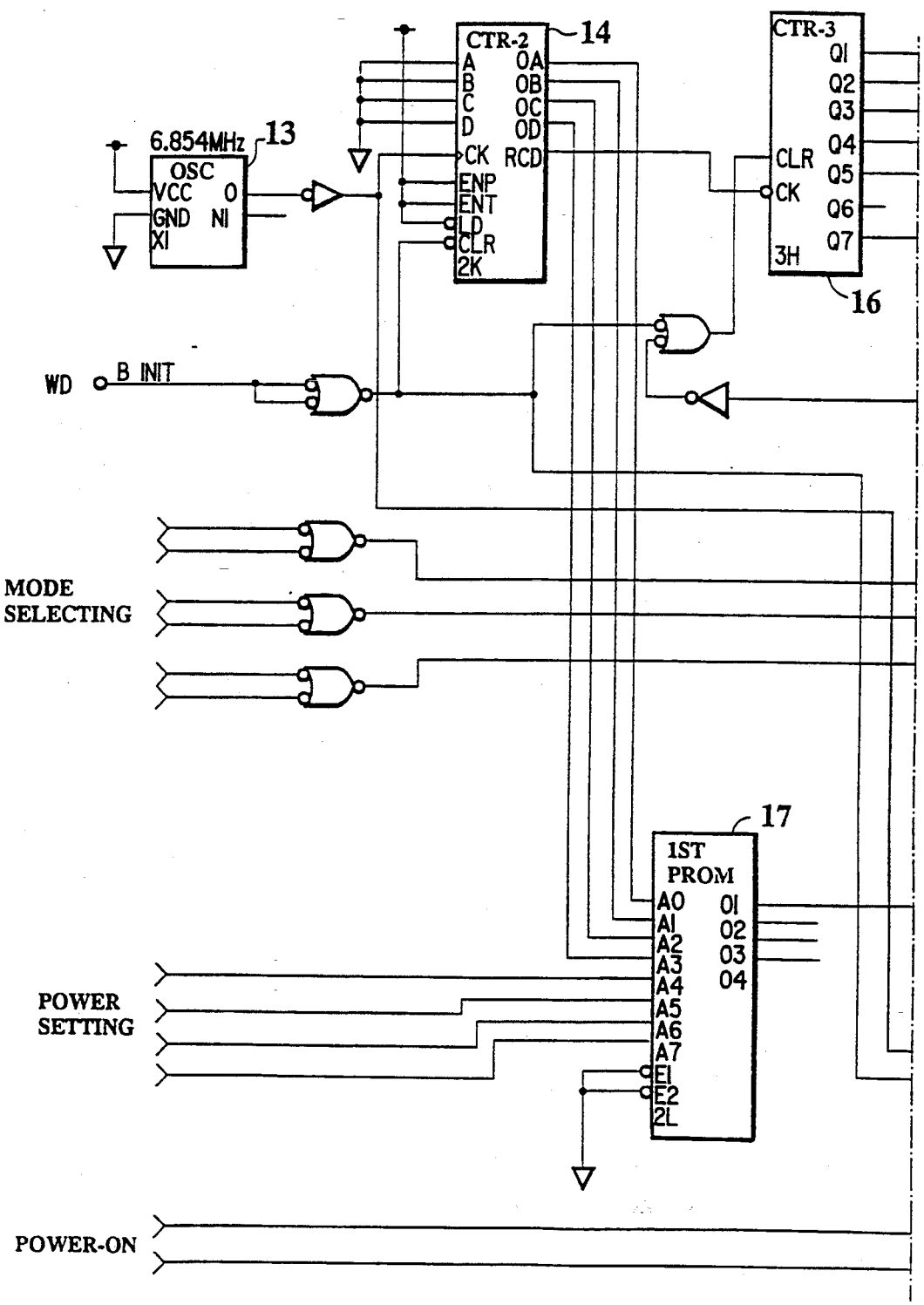
FIGS. 9A and 9B are a circuit diagram of the electrosurgical signal generator 40.
Figure 9B:
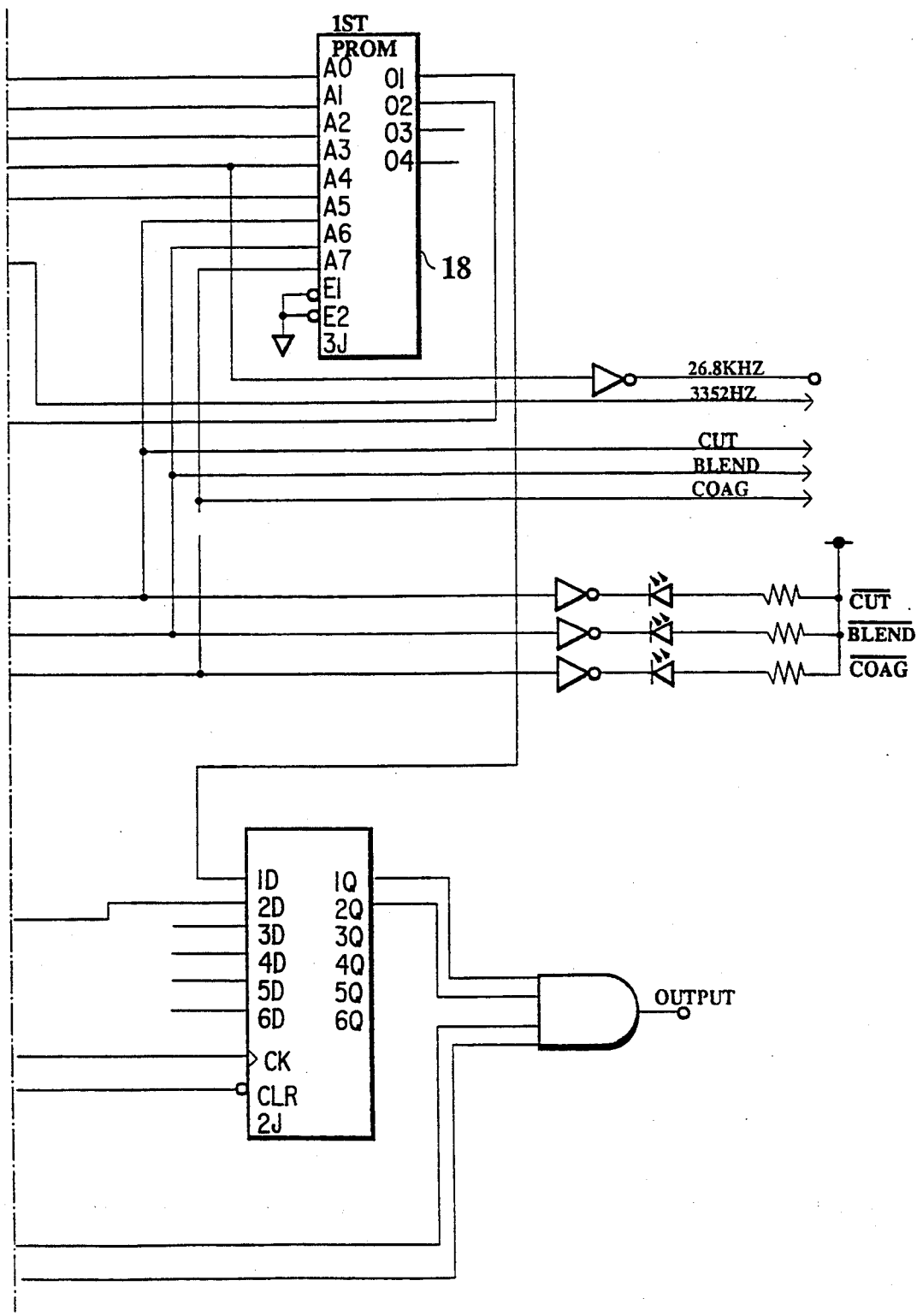

FIGS. 9A and 9B are a practical circuit diagram of the first electrosurgical power supply apparatus 40 shown in FIG. 3.

In the circuit diagram of FIG. 9, the oscillator 13 oscillates a clock having a frequency of 6,854 MHz.

It should be noted that the circuit diagram shown in FIG. 9 represents only a major circuit arrangement of the first electrosurgical power supply apparatus 40, and therefore the first counter 14 has been omitted.

Arrangement of Second Electrosurgical Signal Generator Unit

Figure 10:
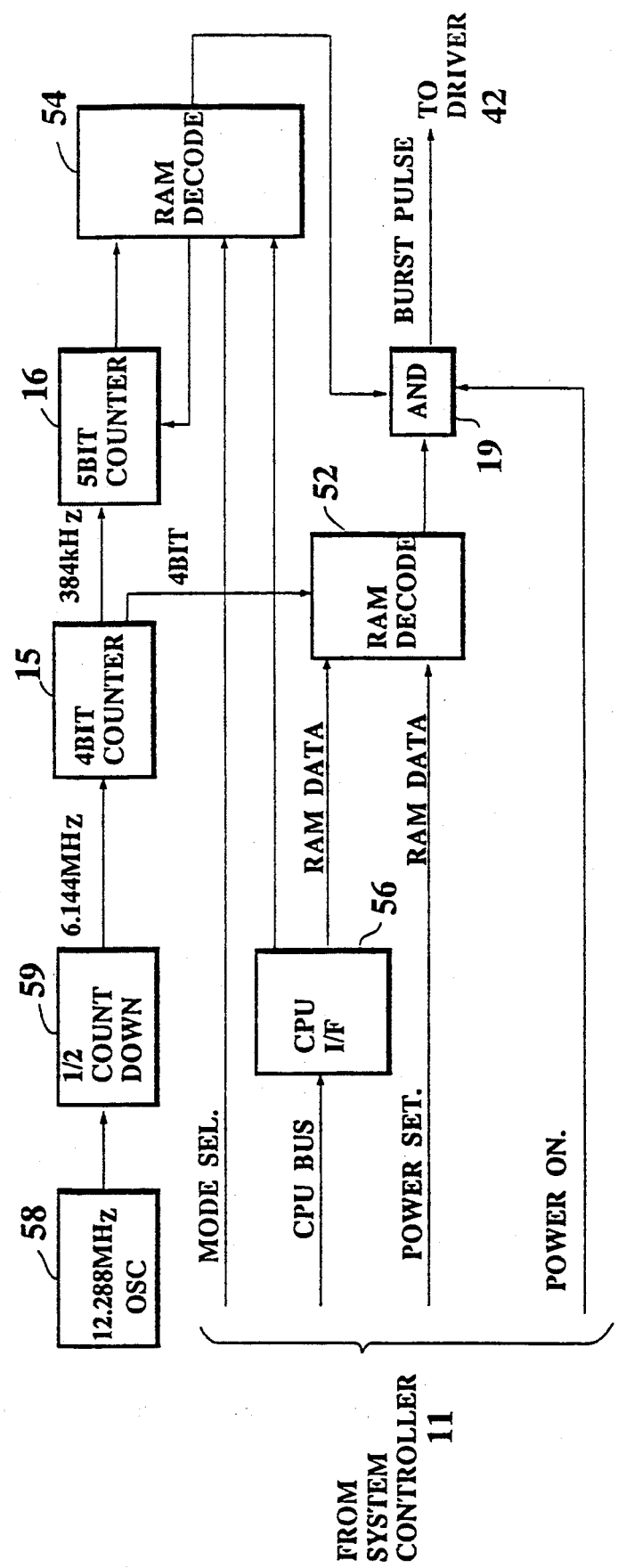
FIG. 10 is a schematic block diagram of another electrosurgical signal generator 50.

FIG. 10 is a schematic block diagram of an electrosurgical signal generator unit 50 employable in the electrosurgical power supply apparatus 20 (see FIG. 2) constructed based upon the first basic idea of the present invention.

A major feature of this electrosurgical signal generator unit 50 is to employ two RAMs (random access memories) 52 and 54 into which two sets of RAM data are supplied from a CPU 56 under control of the system controller 11. An oscillating frequency of an oscillator is selected to be, for instance, 12,288 MHz which is counted down by ½ to obtain a high-frequency clock signal having a frequency of 6,144 MHz, in a first counter 59. As apparent from the foregoing descriptions, these RAM data are similar to the RAM data previously stored into the first and second PROMs 17 and 18.

Arrangement of Third Electrosurgical Signal Generator Unit

Figure 11:
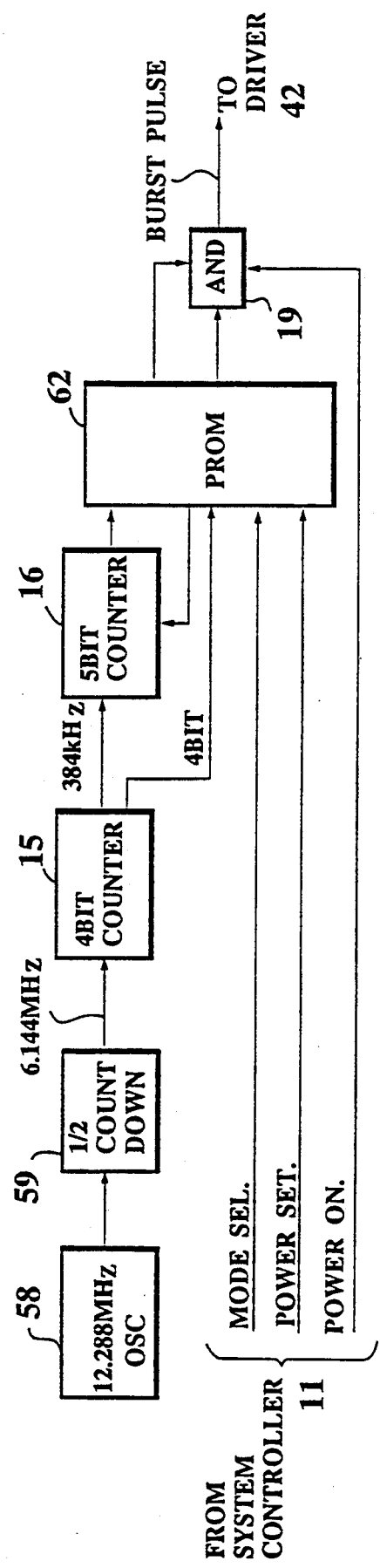
FIG. 11 is a schematic block diagram of a further electrosurgical signal generator 60.

FIG. 11 is a schematic block diagram of an electrosurgical signal generator unit 60 employable in the electrosurgical power supply apparatus 20 constructed based upon the second basic idea of the present invention.

A major feature of this electrosurgical signal generator unit 60 is to employ a single PROM 62 into which ROM data suitable for producing desired high-frequency electrosurgical currents have been previously stored, which are similar to the ROM data stored in the first and second PROMs 17 and 18 shown in FIG. 3.

It should be understood that the present invention is not limited to such electrosurgical power supply apparatuses incorporated into the electronic endoscope apparatus, but may be applied to an electrosurgical power supply apparatus normally used in general surgery.

As previously described, since the electrosurgical power supply apparatus constructed in accordance with the first basic idea of the present invention, employs the electrosurgical signal generator unit for reading out digital (ROM) data from the memory element so as to produce the desirable high-frequency electrosurgical current in a preselected electrosurgical operation mode, the desirable correct current waveform of the high-frequency electrosurgical signal may be supplied to the snare electrode for the electrosurgery purpose with simple and less operation number.

Overall Arrangement of Second Electrosurgical Power Supply Apparatus

Figure 12:
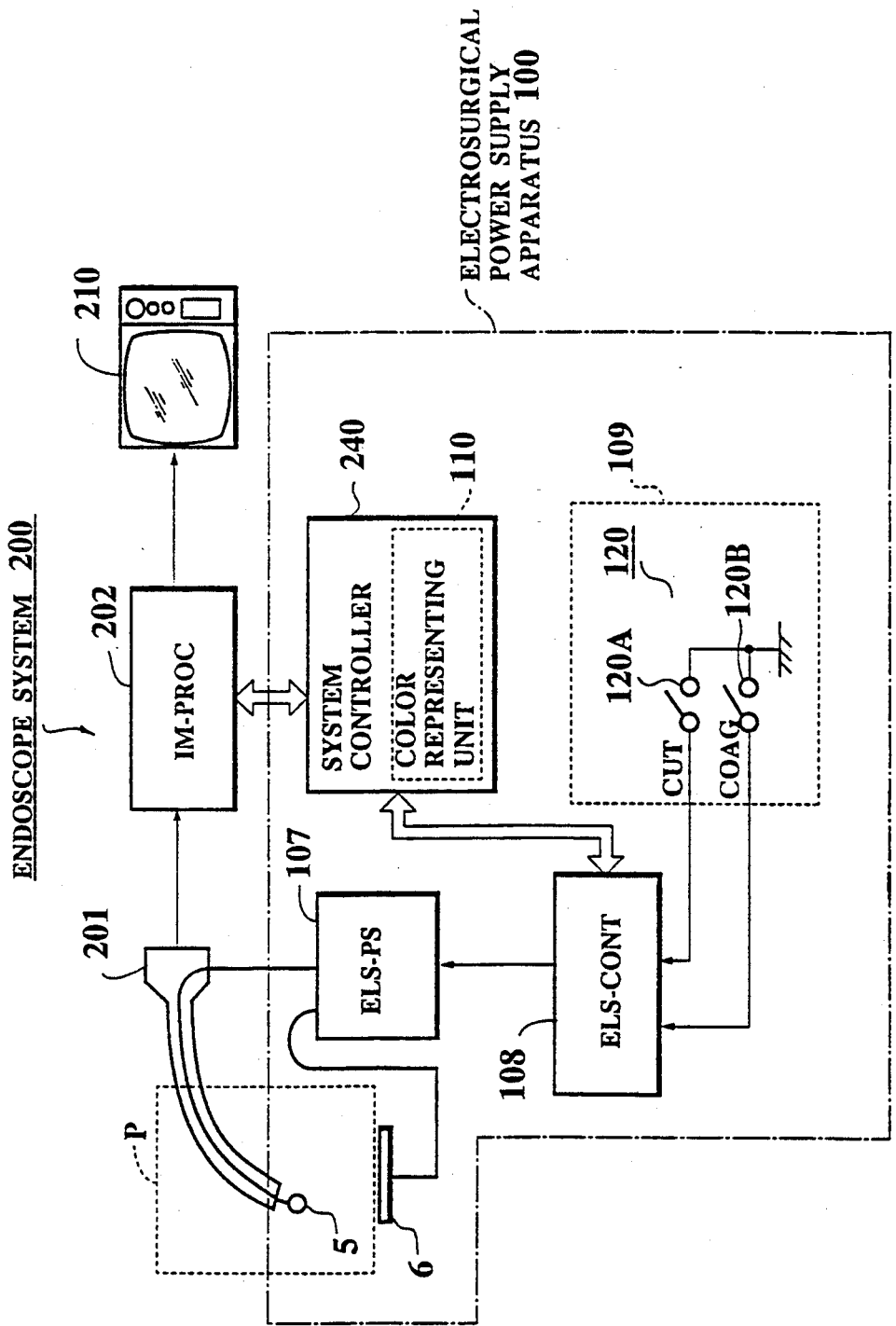
FIG. 12 schematically illustrates a second power supply apparatus 100 for an electrosurgical unit incorporated into an endoscope apparatus, according to another preferred embodiment of the present invention.

FIG. 12 is a schematic block diagram of an electronic endoscope system 200 into which an electrosurgical power supply apparatus 100 constructed in accordance with the second basic idea of the present invention, has been assembled.

In the electronic endoscope system 200, while an insertion portion of an electronic endoscopic scope 201 is conducted into a body cavity of a biological body "P" under medical examination, an image signal obtained from an image sensor 204 (see FIG. 13) of the endoscopic scope 201 is processed so as to construct an endoscopic image of the body cavity in an image signal processor 202, and this endoscopic image is displayed on a color TV monitor 210 under control of a system controller 240. It should be noted that this system controller 240 also has another function to control the electrosurgical power supply apparatus 100 (will be discussed later).

A major arrangement of this electrosurgical power supply apparatus 100 includes an electrosurgical snare electrode 5 and a return electrode 6; a high-frequency electrosurgical current source 107 for supplying a high-frequency electrosurgical current between the snare and return electrodes 5 and 6; an electrosurgery controller 108 for controlling the operation of the high-frequency electrosurgical current source 107; and a mode switch 120 mounted on a display panel 109, for operating the electrosurgery controller 108. The electrosurgical power supply apparatus 100 with the above-described arrangements is incorporated into the above-described electronic endoscope system 200.

As a major feature of this electrosurgical power supply apparatus 100, a color representing unit 110 is included in the system controller 240. A major function of this color representing unit 110 is firstly to visually recognize that either a "cutting" switch 120A or a "coagulation" switch 120B of the mode selecting switch 120 is under operation in response to a signal produced when the mode selecting switch 120 is operated; and secondly to supply an instruction signal to the image signal processor 202, whereby the electrosurgical operation mode selected by the mode selecting switch 120 is displayed in a preselected color representation on the color TV monitor 210. When, for instance, the "cutting" mode or "blend" mode is selected by the mode selecting switch 120, this electrosurgical operation mode is displayed in yellow on the color TV monitor 210. If the "coagulation" mode is selected, the electrosurgical operation mode representation in blue is made on the color TV monitor 210.

Internal Circuit of Color Representing Unit

Figure 13:
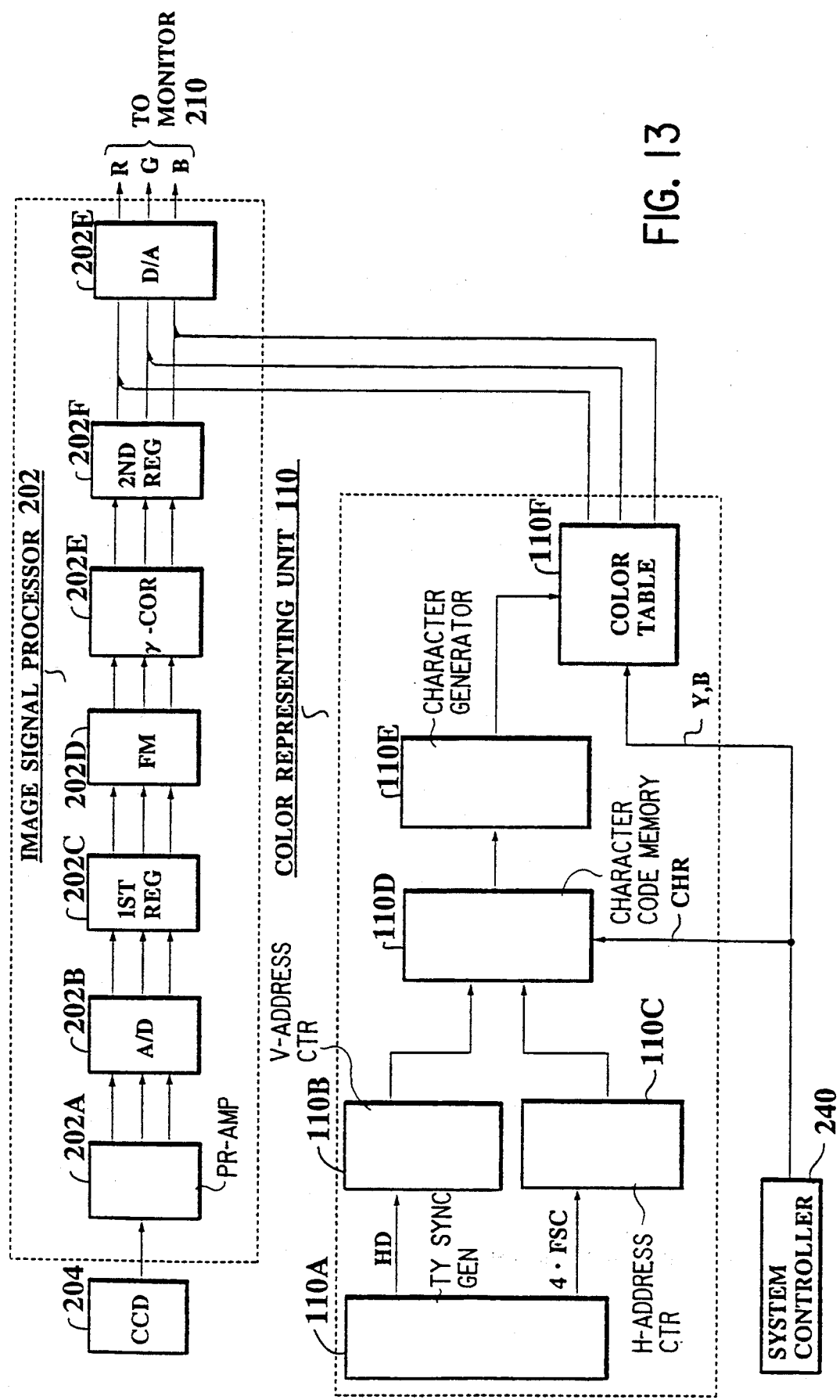
FIG. 13 is a schematic block diagram of an internal circuit of the color representing unit 110 shown in FIG. 12; and, FIG. 14 is an illustration of the display screen of the monitor 210, on which the electrosurgical mode is being displayed.

Referring now to FIG. 13, an internal circuit of the color representing unit 110 shown in FIG. 12 will be summarized.

Before describing the internal circuit of this color representing unit 110, the image sensor 204 and image signal processor 202 will now be summarized. The image signal obtained from the image sensor 204 is amplified in a preamplifier 202A and thereafter A/D-converted in an A/D converter 202B. The digital image data obtained from the A/D converter 202B is temporarily stored in a first register 202C and then stored in a frame memory 202D. The digital image data stored in the frame memory 202D are gamma-corrected in a gamma correcting circuit 202E. The resultant digital image data from the gamma correcting circuit 202E are temporarily stored in a second register 202F and then D/A-converted into a D/A converter 202E, whereby the final image signal is produced from the image signal processor 202 and then supplied to the color TV monitor 210.

On the other hand, the color representing unit 110 is constructed of a TV sync signal generator 110A to supply two sets of sync signals to a vertical address counter 110B and a horizontal address counter 110C. Furthermore, a character code memory 110D is employed to receive two sets of outputs from the vertical address counter 110B and horizontal address counter 110C, and also a character code selecting signal derived from the system controller 240. Then, character code data is read out from the character code memory 110D in response to the character code selecting signal, and thus is supplied to a character generator 110E. A color table 110F is furthermore employed which fetches both character data from the character generator 110E and a color selecting signal from the system controller 240 which is determined by the mode selecting switch 120 shown in FIG. 12.

As a consequence, both the character code representative of the selected electrosurgical operation mode and the selected color data are supplied from the color table 110F to the D/A converter 202E in the image signal processor 202. Thus, the selected electrosurgical operation mode may be displayed in the preselected color on the color TV monitor 210 (will be described in detail).

Color Representation

FIG. 14 illustrates the display screen of the color TV monitor 210 shown in FIG. 12 on which the mode representation, e.g., "CUTTING" is displayed in yellow color. More specifically, the entire display screen is subdivided into a fixed character data region 220 and an arbitrary character data region 230. In the fixed character data region 220, a name of a patient, an age thereof, film number and other data related to the endoscopic diagnosis are written and displayed on the right-hand portion of the monitor screen. In the arbitrary character data region 230, the selected electrosurgical operation mode is written and represented above the endoscopic image of the patient on the left-hand portion of the monitor screen. This electrosurgical operation mode representation is performed by way of the color representing unit 110 in conjunction with the image signal processor 202 shown in FIG. 13.

As apparent from FIG. 14, the fixed character data region 220 is not suitable for writing or representing such an electrosurgical operation mode.

Furthermore, when the blend mode is selected, a character "BLEND" is written into the arbitrary character data region 230 and then displayed above the endoscopic image screen in yellow color instead of the presently displayed "CUTTING", whereas when the coagulation mode is selected, a character "COAGULATION" is written therein and similarly displayed thereon in blue color.

As previously described, according to the electrosurgical power supply apparatus constructed based upon the second basic idea of the present invention, since the electrosurgical operation mode may be visually recognized by way of the above-described color mode representation in response to operations of the mode selecting switch 120 provided on the display panel 109, erroneous operations can be prevented.

As apparent from the foregoing descriptions, the present invention is not limited to the above-described preferred embodiments, but may be modified without departing from the technical scope and spirit of the invention.

For instance, instead of the color made-character representation as shown in FIG. 14, colored waveforms as represented in FIGS. 15A to 15C may be displayed. Alternatively, these colored waveforms may be combined with the color mode-character representation.

Furthermore, the typical color difference signals, e.g., R-Y and B-Y may be utilized instead of three color signals R, B and G as shown in FIG. 13.

While the switches and dials of the electrosurgical power supply apparatus constructed based upon the second basic idea are operated, the selected electrosurgical operation mode is displayed on the color TV monitor. Therefore, there is no risk that the erroneous electrosurgical operation is continued while an operator mistakenly recognizes his designated electrosurgical operation mode.

What is claimed is:

1. An electrosurgical power supply apparatus comprising:
    means for selecting an electrosurgical operation mode to produce a mode selection signal;
    source means for producing an electrosurgical high-frequency signal in response to the mode selection signal; and,
    means for producing a color signal indicative of the electrosurgical operation mode selected by the mode selecting means in response to the mode selection signal, whereby the selected electrosurgical operation mode is represented in a predetermined color, wherein said color signal producing means includes at least:
    character generator means for generating character data indicative of the selected electrosurgical operation mode selected by said selecting means; and
    color table means for previously storing therein color data preselected based upon the electrosurgical operation mode, and for outputting both the character data indicative of the selected electrosurgical operation mode and the color data read therefrom in accordance with the character data indicative of the selected electrosurgical operation mode, whereby a title of the selected electrosurgical operation mode is displayed in a predetermined color defined by the color data.

2. An electrosurgical power supply apparatus as claimed in claim 1, wherein said color signal producing means further includes:
a television synchronization signal generator for generating both a horizontal synchronization signal and a vertical synchronization signal so as to display the title of the selected electrosurgical operation mode on a television monitor.

3. An electrosurgical power supply apparatus as claimed in claim 1, wherein said color signal producing means produces a plurality of color signals representative of pictorial forms with preselected colors in accordance with the selected mode signals.

4. An electrosurgical power supply apparatus as claimed in claim 1, wherein said selecting means is constructed of a plurality of switches.

5. An electrosurgical power supply apparatus in combination with and for supplying power to an electronic endoscope system including at least image sensor means for producing an image signal of an interior of an internal organ under medical examination; image signal processing means for processing the image signal to obtain an endoscopic image signal; and a color television monitor connected with said image signal processing means for displaying an endoscopic image of an object in response to the endoscopic image signal, comprising:
means for selecting an electrosurgical operation mode to produce a mode selection signal;
source means for producing an electrosurgical high-frequency signal in response to the mode selection signal;
means for producing a color signal representative of the electrosurgical operation mode selected by the mode selecting means in response to the mode selection signal and for supplying the color signal to the color television monitor; whereby the selected electrosurgical operation mode is displayed on the television monitor in a predetermined color together with the endoscopic image of the object.

6. An electrosurgical power supply apparatus combined with an electronic endoscope system as claimed in claim 5, wherein said color signal producing means includes at least:
character generator means for generating character data indicative of a title of the selected electrosurgical operation mode;
color table means for previously storing therein color data preselected based upon the selected electrosurgical operation modes, and for outputting both the character data indicative of the selected electrosurgical operation mode and the color data read therefrom in accordance with the character data indicative of the selected electrosurgical operation mode, whereby a title of the selected electrosurgical operation mode is displayed in a predetermined color defined by the color data on the color television monitor.

7. An electrosurgical power supply apparatus combined with an electronic endoscope system as claimed in claim 6, wherein said color signal producing means further includes:
a television synchronization signal generator for generating both a horizontal synchronization signal and a vertical synchronization signal in order to display title of the selected electrosurgical operation mode on the color television monitor.

8. An electrosurgical power supply apparatus in combination with and for supplying electric power to an electronic endoscope system including at least image sensor means for producing an image signal of an interior of a subject under medical examination; image signal processing means for processing the image signal to obtain an endoscopic image signal; and a color television monitor connected to said image signal processing means for displaying an endoscopic image of the interior of the subject in response to the endoscopic image signal, comprising:
means for selecting an electrosurgical operation mode to produce a mode selection signal;
source means for producing an electrosurgical high-frequency signal in response to the mode selection signal;
means for producing a visual signal representative of the electrosurgical operation mode selected by the mode selecting means in response to the mode selection signal and for supplying the visual signal to the color television monitor; whereby the selected electrosurgical operation mode is displayed on the television monitor in a predetermined color together with the endoscopic image of the subject.

9. An electrosurgical power supply apparatus as claimed in claim 8 wherein said operational modes include coagulation, cutting and blend.

10. An electrosurgical power supply apparatus as claimed in claim 8 wherein said visual signal is a color signal.

11. An electrosurgical power supply apparatus as claimed in claim 8 wherein said operational modes include coagulation, cutting and blend.

* * * * *